US009217735B2

(12) United States Patent
Joshi et al.

(10) Patent No.: US 9,217,735 B2
(45) Date of Patent: Dec. 22, 2015

(54) SELECTING AN IMPROVED CATALYST COMPOSITION AND HYDROCARBON CONVERSION PROCESS USING SAME

(75) Inventors: Yogesh V. Joshi, Annandale, NJ (US); Pallassana S. Venkataraman, Annandale, VA (US); Terry E. Helton, Bethlehem, PA (US); Charles M. Smith, Houston, TX (US); Jose G. Santiesteban, Hellertown, PA (US); Matthew J. Vincent, Kingwood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 73 days.

(21) Appl. No.: 13/704,443

(22) PCT Filed: Aug. 4, 2011

(86) PCT No.: PCT/US2011/046587
§ 371 (c)(1),
(2), (4) Date: May 24, 2013

(87) PCT Pub. No.: WO2012/050655
PCT Pub. Date: Apr. 19, 2012

(65) Prior Publication Data
US 2013/0253246 A1 Sep. 26, 2013

Related U.S. Application Data

(60) Provisional application No. 61/393,651, filed on Oct. 15, 2010.

(51) Int. Cl.
C07C 2/66 (2006.01)
G01N 31/10 (2006.01)
B01J 29/70 (2006.01)
B01J 29/08 (2006.01)

(52) U.S. Cl.
CPC ............ *G01N 31/10* (2013.01); *B01J 29/08* (2013.01); *B01J 29/70* (2013.01); *B01J 29/7007* (2013.01); *B01J 29/7038* (2013.01); *C07C 2/66* (2013.01); *C07C 2529/08* (2013.01); *C07C 2529/70* (2013.01)

(58) Field of Classification Search
CPC ...................................................... C07C 2/66
USPC ........................................................ 585/467
See application file for complete search history.

(56) References Cited

U.S. PATENT DOCUMENTS

| 3,751,504 | A | 8/1973 | Keown et al. |
| 4,016,218 | A | 4/1977 | Haag et al. |
| 4,547,605 | A | 10/1985 | Kresge et al. |
| 4,549,426 | A | 10/1985 | Erickson |
| 4,891,458 | A | 1/1990 | Innes et al. |
| 4,992,606 | A | 2/1991 | Kushnerick et al. |
| 5,003,119 | A | 3/1991 | Sardina et al. |
| 5,034,563 | A | 7/1991 | Ashjian et al. |
| 5,191,135 | A | 3/1993 | Dwyer et al. |
| 5,334,795 | A | 8/1994 | Chu et al. |
| 5,557,024 | A | 9/1996 | Cheng et al. |
| 5,600,048 | A | 2/1997 | Cheng et al. |
| 5,600,050 | A | 2/1997 | Huang et al. |
| 5,959,168 | A | 9/1999 | van der Aalst et al. |
| 6,376,730 | B1 | 4/2002 | Jan et al. |
| 6,984,764 | B1 | 1/2006 | Roth et al. |
| 7,038,100 | B2 | 5/2006 | Dandekar et al. |
| 7,411,101 | B2 | 8/2008 | Chen et al. |
| 7,645,913 | B2 | 1/2010 | Clark et al. |
| 7,649,122 | B2 | 1/2010 | Clark et al. |
| 7,655,824 | B2 | 2/2010 | Riley et al. |
| 2002/0137977 | A1 | 9/2002 | Hendriksen et al. |
| 2004/0138051 | A1 | 7/2004 | Shan et al. |
| 2005/0197517 | A1 | 9/2005 | Cheng et al. |
| 2007/0179329 | A1 | 8/2007 | Clark |
| 2008/0154080 | A1 | 6/2008 | Kalyanoraman et al. |
| 2008/0287720 | A1 | 11/2008 | Clark |
| 2009/0137855 | A1 | 5/2009 | Clark et al. |
| 2009/0234169 | A1 | 9/2009 | Pelati et al. |

FOREIGN PATENT DOCUMENTS

| EP | 0 293 032 | 11/1988 |
| EP | 0 847 802 | 11/2004 |
| WO | WO 2006/002805 | 1/2006 |

OTHER PUBLICATIONS

D. Zhou et al., "DFT Studies on the location and acid strength of Bronsted acid sites in MCM-22 zeolite", Journal of Molecular Catalysis A: Chemical 244 (2006) pp. 11-19.

J. C. Cheng et al., "A Comparison of Zeolites MCM-22, Beta, and USY for Liquid Phase Alkylation of Benzene with Ethylene", Science and Technology in Catalysis, (1998), pp. 53-60.

T. F. Degnan, "The implication of the fundamentals of shape selectivity for the development of catalysts for the petroleum and petrochemical industries", J. Catalysis, 216 (2003), pp. 32-46, Fig. 2 and Section 6.

R. Millini et al., Microporous Materials 4 (1995), pp. 221.

G. Bellussi et al., J. Catalysis 157 (1995), pp. 227.

(Continued)

Primary Examiner — Thuan D Dang
(74) Attorney, Agent, or Firm — Siwen Chen; Stephen A. Baehl

(57) ABSTRACT

The present invention provides a method for selecting an improved catalyst composition comprising a crystalline molecular sieve material having a structure and properties whereby the catalyst composition has at least one active catalytic site with a Mono Alkylation Selectivity Factor (MASF) greater than or equal to 0 kcal/mol±0.5 kcal/mol, and optionally further at least one active catalytic site with an Olefin Oligomerization Suppression Factor (OOSF) greater than or equal to 5 kcal/mol±0.5 kcal/mol. Further, there is provided an improved process for conversion of hydrocarbon feedstock in the presence of said selected catalyst composition.

18 Claims, No Drawings

(56) References Cited

OTHER PUBLICATIONS

Y. Wang et al., "Density Functional Theory Study of Proton Hopping in MCM-22 zeolite", Chemical Physics Letters, 388 (2004), pp. 363-366.

D. Zhou et al., "DFT study of the acid strength of MCM-22 with double Si/Al substitutions in 12MR supercage", Journal of Molecular Structure, THEOCHEM 756, (2005), pp. 39-46.

Carlo Perego et al., "Recent Advances in the industrial alkylation of aromatics: new catalysts and new processes," Catalysis Today 73, (2002), pp. 3-22.

R. Rungsirisakun et al., "Adsorption and diffusion of benzene in the nanoporous catalysts FAU, ZSM-5, and MCM-22: A Molecular Dynamics Study", Journal of Molecular Graphics and Modeling, vol. 24, (2006), pp. 373-382.

A. Corma et al., "Alkylation of Benzene with Short-Chain Olefins Over MCM-22 Zeolite: Catalytic Behaviour and Kinetic Mechanism", J. of Catalysis, 192, (2000), pp. 163-173.

SELECTING AN IMPROVED CATALYST COMPOSITION AND HYDROCARBON CONVERSION PROCESS USING SAME

PRIORITY CLAIM

This application is a National Stage Application of International Application No. PCT/US2011/046587 filed Aug. 4, 2011, which claims priority U.S. Provisional Application Ser. No. 61/393,651 filed Oct. 15, 2010, both of which are fully incorporated herein by their reference.

BACKGROUND OF THE INVENTION

The present invention relates to a method for selecting an improved catalyst composition and a hydrocarbon compound conversion process utilizing the catalyst selected.

The improved catalyst composition selected by the present invention comprises a crystalline molecular sieve material having a structure and properties whereby the catalyst composition has at least one active catalytic site with a Mono Alkylation Selectivity Factor (hereinafter more particularly described) greater than or equal to 0 kcal/mol±0.5 kcal/mol, and optionally further at least one active catalytic site with an Olefin Oligomerization Suppression Factor (hereinafter more particularly described) greater than or equal to 5±0.5 kcal/mol.

The method of the present invention for selecting an improved catalyst composition comprising a porous crystalline material for use in a hydrocarbon conversion process comprises the steps of determining the Mono Alkylation Selectivity Factor of one or more catalyst compositions, and selecting a catalyst composition which has at least one active catalytic site with a Mono Alkylation Selectivity Factor greater than or equal to 0 kcal/mol±0.5 kcal/mol. The method may further comprise the steps of determining the Olefin Oligomerization Suppression Factor of one or more catalyst compositions, and selecting a catalyst composition which has at least one active catalytic site with an Olefin Oligomerization Suppression Factor greater than or equal to 5 kcal/mol±0.5 kcal/mol. The selected improved catalyst is beneficially selective and may be used to effect various chemical conversions, and is particularly valuable for use in an alkylation process for producing alkylaromatics, particularly ethylbenzene and cumene.

Of the alkylaromatic compounds advantageously produced by the present process utilizing the selected catalyst, ethylbenzene and cumene, for example, are valuable commodity chemicals which are used industrially for the production of styrene monomer and coproduction of phenol and acetone, respectively. In fact, a common route for the production of phenol comprises a process which involves alkylation of benzene with propylene to produce cumene, followed by oxidation of the cumene to the corresponding hydroperoxide, and then cleavage of the hydroperoxide to produce equimolar amounts of phenol and acetone. Ethylbenzene may be produced by a number of different chemical processes. One process which has achieved a significant degree of commercial success is the vapor phase alkylation of benzene with ethylene in the presence of a solid, acidic, ZSM-5 zeolite catalyst. Examples of such ethylbenzene production processes are described in U.S. Pat. No. 3,751,504 (Keown), U.S. Pat. No. 4,547,605 (Kresge) and U.S. Pat. No. 4,016,218 (Haag). U.S. Pat. No. 5,003,119 (Sardina) describes the use of zeolites X, Y, L, Beta, ZSM-5, Omega, and mordenite and chabazite in the synthesis of ethylbenzene. U.S. Pat. No. 5,959,168 (van der Aalst) describes the use of zeolites Y, Beta, MCM-22, MCM-36, MCM-49 and MCM-56 in the synthesis of ethylbenzene in a plant designed for use of aluminum chloride-based catalyst.

Another process which has achieved significant commercial success is the liquid phase alkylation for producing ethylbenzene from benzene and ethylene, since it operates at a lower temperature than the vapor phase counterpart, and hence tends to result in lower yields of by-products. For example, U.S. Pat. No. 4,891,458 (Innes) describes the liquid phase synthesis of ethylbenzene with zeolite beta, whereas U.S. Pat. No. 5,334,795 (Chu) describes the use of MCM-22 in the liquid phase synthesis of ethylbenzene; and U.S. Pat. No. 7,649,122 (Clark) describes the use of MCM-22 in the liquid phase synthesis of ethylbenzene in the presence of a maintained water content. U.S. Pat. No. 4,549,426 (Inwood) describes the liquid phase synthesis of alkylbenzene with steam stabilized zeolite Y. U.S. Patent Publication No. 2009/0234169 A1 (Pelati) describes the liquid phase aromatic alkylation over at least one catalyst bed containing a first catalyst modified by inclusion of a rare earth metal ion.

Cumene has been produced commercially by the liquid phase alkylation of benzene with propylene over a Friedel-Craft catalyst, particularly solid phosphoric acid or aluminum chloride. Zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Other publications show the use of catalysts comprising crystalline zeolites for the conversion of feedstock comprising an alkylatable aromatic compound and an alkylating agent to alkylaromatic conversion product under at least partial liquid phase conversion conditions. These include U.S. 2005/0197517A1 (Cheng); U.S. 2002/0137977A1 (Hendrickson); and U.S. 2004/0138051A1 (Shan) showing the use of a catalyst comprising a microporous zeolite embedded in a mesoporous support; WO 2006/002805 (Spano); and U.S. Pat. No. 6,376,730 (Jan) showing the use of layered catalyst; EP 0847802B1; and U.S. Pat. No. 5,600,050 (Huang) showing the use of catalyst comprising 30 to 70 wt. % H-Beta zeolite, 0.5 to 10 wt. % halogen, and the remainder alumina binder.

Other such publications include U.S. Pat. No. 5,600,048 (Cheng) describing preparing ethylbenzene by liquid phase alkylation over acidic solid oxide, such as MCM-22, MCM-49, MCM-56, Beta, X, Y or mordenite; U.S. Pat. No. 7,411,101 (Chen) describing preparing ethylbenzene or cumene by liquid phase alkylation over acidic solid oxide, such as PSH-3, ITQ-2, MCM-22, MCM-36, MCM-49, MCM-56 and Beta at conversion conditions including a temperature as high as 482° C. and pressure as high as 13,788 kPa; and U.S. Pat. No. 7,645,913 (Clark) describing preparing alkylaromatic compounds by liquid phase alkylation in a multistage reaction system over acidic solid oxide catalyst in the first reaction zone having more acid sites per unit volume of catalyst than the catalyst in the second reaction zone at conversion conditions including for ethylbenzene a temperature as high as 270° C. and pressure as high as 8,300 kPa, and for cumene a temperature as high as 250° C. and pressure as high as 5,000 kPa. U.S. Patent Publication No. 2008/0287720 (Clark) describes alkylation of benzene over catalyst of the MCM-22 family material in a reaction zone having water content maintained at from 1 to 900 wppm. U.S. Patent Publication No. 2009/0137855 (Clark) describes a mixed phase process for producing alkylaromatic compounds from a dilute alkene feedstock which also includes alkane impurities. In the latter publication, the volume ratio of liquid to vapor in the feedstock is from 0.1 to 10.

Existing alkylation processes for producing alkylaromatic compounds, for example, ethylbenzene and cumene, inherently produce polyalkylated species as well as the desired monoalkyated product. It is therefore normal to transalkylate the polyalkylated species with additional aromatic feed, for example benzene, to produce additional monoalkylated product, for example ethylbenzene or cumene, either by recycling the polyalkylated species to the alkylation reactor or, more frequently, by feeding the polyalkylated species to a separate transalkylation reactor. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-49, MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764.

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional monoalkylated product without producing unwanted by-products. This has proven to be a significant problem in the case of cumene production where existing catalysts have either lacked the desired activity or have resulted in the production of significant quantities of by-products such as ethylbenzene and n-propylbenzene.

Although it is suggested in the art that catalysts for conversion of feedstock comprising an alkylatable aromatic compound and an alkylating agent to alkylaromatic conversion product under at least partial liquid phase conversion conditions are composed of a porous crystalline aluminosilicate molecular sieves having an MWW structure type, the present catalyst selection method and improved process has remained elusive. Selecting a commercially acceptable catalyst for such processes conducted under at least partial liquid phase conversion conditions which increases monoselectivity, i.e., providing lower di- or polyalkyl product make, and does not significantly affect conversion would allow capacity expansion in existing plants and lower capital expense for grass-roots plants. Unfortunately, the pore size and shape of crystalline molecular sieve components of catalyst compositions cannot adequately explain which catalyst compositions function as most effective selective aromatic alkylation catalysts. According to the present invention, it has now unexpectedly been found that an alkylation process for producing alkylaromatics conducted in the presence of a specific catalyst, selected by the present method, comprising a porous crystalline molecular sieve material, e.g., a crystalline aluminosilicate zeolite ("crystal"), having a structure and properties, whereby the catalyst composition has at least one active catalytic site with a Mono Alkylation Selectivity Factor greater than or equal to 0 kcal/mol±0.5 kcal/mol, and optionally further at least one active catalytic site with an Olefin Oligomerization Suppression Factor greater than or equal to 5 kcal/mol±0.5 kcal/mol, yields a unique combination of activity and monoselectivity. This is especially the case when the process involves at least partial liquid phase alkylation for manufacture of ethylbenzene or cumene.

SUMMARY OF THE INVENTION

According to the present invention, there is provided a method for selecting an improved catalyst composition comprising a crystalline molecular sieve material having a structure and properties, whereby the catalyst composition has at least one active catalytic site with a Mono Alkylation Selectivity Factor greater than or equal to 0 kcal/mol±0.5 kcal/mol, and optionally further at least one active catalytic site with an Olefin Oligomerization Suppression Factor greater than or equal to 5 kcal/mol±0.5 kcal/mol. Further, there is provided an improved process for conversion of hydrocarbon feedstock in the presence of said selected catalyst composition. An embodiment of such a conversion process comprises converting an alkylatable aromatic compound and an alkylating agent to desired alkylaromatic conversion product, such as under at least partial liquid phase conversion conditions, in the presence of the specific selected catalyst composition. The selected catalyst composition allows for high, selective conversion of feedstock to highly desirable product at commercially beneficial reaction conditions.

According to one embodiment of the invention, there is provided a method for selecting a catalyst composition comprising a porous crystalline material for use in a hydrocarbon conversion process, said method comprising steps of determining the Mono Alkylation Selectivity Factor of one or more catalyst compositions, and selecting a catalyst composition which has at least one active catalytic site with a Mono Alkylation Selectivity Factor greater than or equal to 0 kcal/mol±0.5 kcal/mol. In another embodiment, the method for selecting a catalyst further comprises steps of determining the Olefin Oligomerization Suppression Factor of one or more catalyst compositions, and selecting a catalyst composition which has at least one active catalytic site with an Olefin Oligomerization Suppression Factor greater than or equal to 5 kcal/mol±0.5 kcal/mol.

According to another embodiment of the invention, there is provided a catalyst composition comprising a porous crystalline material, said composition having at least one active catalytic site with a Mono Alkylation Selectivity Factor greater than or equal to 0 kcal/mol, such as greater than or equal to 7.5 kcal/mol. In another embodiment of the invention, there is provided a catalyst composition further having at least one active catalytic site with an Olefin Oligomerization Suppression Factor greater than or equal to 5 kcal/mol, such as greater than or equal to 11.4 kcal/mol.

According to another embodiment of the invention, there is provided a process for selectively producing a desired monoalkylated aromatic compound comprising the step of contacting an alkylatable aromatic compound with an alkylating agent in the presence of a catalyst composition under at least partial liquid phase conditions, said catalyst composition having at least one active catalytic site with a Mono Alkylation Selectivity Factor greater than or equal to 0 kcal/mol. Another embodiment of the present invention is an improved alkylation process for the selective production of monoalkyl benzene comprising the step of reacting benzene with an alkylating agent such as ethylene or propylene under alkylation conditions in the presence of a catalyst composition which comprises a porous crystalline material, e.g., a crystalline aluminosilicate, said catalyst composition having at least one active catalytic site with a Mono Alkylation Selectivity Factor greater than or equal to 0 kcal/mol.

The catalyst composition selected for use in the present improved process comprises a crystalline molecular sieve having a structure and properties which provide the catalyst composition with the requisite Mono Alkylation Selectivity Factor and optionally Olefin Oligomerization Suppression Factor. Non-limiting examples of desirable crystalline molecular sieves which can be manufactured and evaluated by the present method and, if selected, used in the present catalytic conversion process including those of a MWW structure type.

Molecular sieves of MWW structure type generally have an X-ray diffraction pattern including d-spacing maxima at 12.4±0.25, 6.9±0.15, 3.57±0.07 and 3.42±0.07 Angstroms. The X-ray diffraction data used to characterize the material are obtained by standard techniques using the K-alpha doublet of copper as the incident radiation and a diffractometer equipped with a scintillation counter and associated computer as the collection system. Molecular sieves of MWW structure type include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697); and UZM-8 (described in U.S. Pat. No. 6,756,030). Preferably, the molecular sieve for the catalyst herein is selected from MCM-49, MCM-56 and isotypes of MCM-49 and MCM-56, such as ITQ-2.

DETAILED DESCRIPTION OF THE INVENTION

More particularly, the present invention relates to a method for selecting an improved catalyst composition and process utilizing the selected catalyst for production of monoalkylated aromatic compounds, particularly ethylbenzene and cumene, by the liquid or partial liquid phase alkylation of an alkylatable aromatic compound, for example benzene. In various embodiments, this type of catalyst can be useful for hydroalkylating benzene to cyclohexylbenzene (CHB), such as when formulated a hydrogenation metal (e.g., palladium) and optionally supported on, or impregnated within, an inorganic oxide. The catalyst may comprise 0.05 to 10 wt. %, or 0.1 to 5 wt. %, of hydrogenation metal based upon total weight of the catalyst. Hydroalkylation techniques, methods for forming hydroalkylation catalysts and suitable hydrogenation metals and inorganic oxides are disclosed in PCT App. No. PCT/US2011/042161, which is incorporated by reference for this purpose.

The method for selecting an improved catalyst composition evaluates critical properties of the composition required to achieve high aromatic alkylation selectivity. These properties are related to the free energy of adsorption and co-adsorption of the various reactants. The pore size and shape of crystalline molecular sieve components of catalyst compositions do not adequately explain which catalyst compositions are most effective selective aromatic alkylation catalysts.

Not intending to be bound by a theory of operation, we believe that molecular modeling shows that in highly desirable molecular sieves, the co-adsorption of cumene and propylene is significantly less favorable compared to the co-adsorption of the benzene and propylene. The calculated free energy for co-adsorption of propylene and cumene ($^T\Delta G_{Co\text{-}Ads}^{Propylene+Cumene}$) is less thermodynamically favorable compared to the calculated ($^T\Delta G_{Co\text{-}Ads}^{Propylene+Benzene}$) for propylene and benzene. This would limit the subsequent alkylation of cumene over catalysts comprising the same. Thus, the proposed attribute for this beneficial selectivity is termed Mono Alkylation Selectivity Factor ("MASF"). This is defined by the formula:

$$\text{MASF} = {}^T G_{Co\text{-}Ads}^{Olefin+MonoAlkylated\ Aromatics} - {}^T\Delta G_{Co\text{-}Ads}^{Olefin+Aromatics},$$

wherein T is temperature in ° C., and $^T\Delta G_{Co\text{-}Ads}^{A+B}$ is the free energy of co-adsorption (i.e., "Co-Ads") of olefin A (e.g., propylene) and aromatic B (e.g., cumene or benzene) in kcal/mol, calculated as described below.

For some aromatic alkylation reactions, oligomerization of an olefin alkylating agent is a deleterious side reaction which results in loss of olefin selectivity and catalyst fouling. Calculations also indicate that for highly desirable molecular sieves, the adsorption of olefins such as propylene is much weaker as compared to the adsorption of aromatic molecules such as benzene. The difference between the calculated free energy of adsorption of propylene ($^T\Delta G_{Ads}^{Propylene}$) and that of benzene ($^T\Delta G_{Ads}^{Benzene}$) is very high for such materials. The strong adsorption of benzene relative to propylene lowers the probability of co-adsorption of two propylene molecules at adjacent sites on the surface, and mitigates the likelihood of olefin-olefin oligomerization reactions. Materials which have a thermodynamically more favorable ΔG of adsorption of benzene relative to olefin, should exhibit less olefin oligomerization. The olefin selectivity can thus be characterized by an Olefin Oligomerization Suppression Factor ("OOSF"). This is defined by the formula:

$$\text{OOSF} = {}^T\Delta G_{Ads}^{Olefin} - {}^T\Delta G_{Ads}^{Aromatics},$$

wherein T is temperature in ° C., and $^T\Delta G_{Ads}^{A}$ is free energy of adsorption (i.e., "Ads") of molecule A (e.g., olefin or aromatic) in kcal/mol, calculated as described below.

In the above formulae for MASF and OOSF, temperature T is, for example, from 100° C. to 300° C., preferably chosen to be the same or essentially the same as the temperature to be maintained in the hydrocarbon conversion process in which the selected catalyst composition will be used. For example, if the hydrocarbon conversion process will be alkylation of benzene with ethylene at 200° C., then MASF and/or OOSF would preferably be determined at about 200° C. Further, temperature T should be the same for determining MASF and/or OOSF for each of the catalyst compositions being evaluated. For example, if three catalyst compositions are being evaluated for their MASF values, then T would be the same for each evaluation.

MASF is the key attribute for aromatic alkylation selectivity, and OOSF is a secondary attribute relevant to alkylation chemistries where olefin oligomerization is an issue. Therefore, a most beneficial selective aromatic alkylation catalyst is defined by the following attribute:

a. preferred alkylation catalysts will have at least one site with MASF greater than or equal to 0 kcal/mol±0.5 kcal/mol,
b. more preferred alkylation catalysts will have at least one site with MASF greater than or equal to 3 kcal/mol±0.5 kcal/mol, and
c. most preferred alkylation catalyst will have at least one site with MASF greater than or equal to 7 kcal/mol±0.5 kcal/mol.

A most beneficial selective alkylation catalyst which suppresses olefin oligomerization is defined by the following attribute:

a. preferred alkylation catalysts will have at least one site with OOSF greater than or equal to 5 kcal/mol±0.5 kcal/mol,
b. more preferred alkylation catalysts will have at least one site with OOSF greater than or equal to 7 kcal/mol±0.5 kcal/mol, and
c. most preferred alkylation catalyst will have at least one site with OOSF greater than or equal to 10 kcal/mol±0.5 kcal/mol.

The molecular modeling we use is the hybrid QM/MM method described in Frisch, M. J. et al. Gaussian 03; Revision D.01; Gaussian, Inc.: Wallingford Conn., 2004, incorporated herein by reference. This method combines an accurate quantum mechanical method (QM) such as DFT and fast molecular mechanics method (MM). The calculations are done using a cluster model. For example, in a zeolite crystal structure there are symmetrically nonequivalent tetrahedral framework positions known as T-sites. An isoelectronic substitution of the framework Si by Al⁻ (aluminum anion) requires charge compensating extraframework cations. These extraframework cations serve as active catalytic sites for several reactions. For hybrid QM/MM calculations, we use embedded cluster models. They consist of two layers. The innermost layer, called "model geometry", consists of a limited number of T-sites (e.g., about 15) and hydrocarbon species treated with a more accurate level of theory. The T-sites selected for the inner layer are up to a second nearest neighbor for the framework Al. The outer layer consists of a large number of T-sites (e.g., about 185) located symmetrically around the inner layer. Thus, in total, the embedded cluster (EC) consists of about 200 T-sites. This cluster represents the complete feature of the zeolite framework. It could be a pore or cross-section or surface pocket, which is important in order to account for the shape selective effects of the zeolite framework. This large cluster is classically termed as the "real geometry". The outer layer of the embedded cluster is terminated with Si—H bonds with Si—H distance fixed at 1.47 Å.

All the atoms from the inner layer, including hydrocarbon molecules, are completely optimized while atoms from the outer layer are fixed to their crystallographic position. For all calculations, default convergence criteria of 0.00063 Å for average displacement and 0.35 kcal/Å for average gradient are employed.

The embedding scheme we use for the hybrid method is a two layer ONIOM method described in Dapprich, S., Komaromi, I., Byun, K. S., Morokuma, K., Frisch, M. J.; J. Mol. Struct.-Theochem 1999, 462, 1, incorporated herein by reference. It is an extrapolation scheme which makes use of two levels of theories, namely high level and low level. We use density functional theory as the high level of theory. The density functional consists of Becke three parameter (Becke, A. D.; J. Chem. Phys. 1993, 98, 5648, incorporated herein by reference) hybrid exchange functional, with the Lee, Yang and Parr correlation functional (Lee, C., Yang, W., Parr, R. G.; Phys. ReV. B 1988, 37, 785, incorporated herein) termed as B3LYP. The basis set we use for higher level theory is a 6-31 g (d, p) double-ζ basis set (Francl, M. M., Pietro, W. J., Hehre, W. J., Binkley, J. S., Gordon, M. S., DeFrees, D. J., Pople, J. A.; J. Chem. Phys. 1982, 77, 3654, incorporated herein by reference). Molecular mechanics using the universal force field (UFF) (Rappe, A. K., Casewit, C. J., Colwell, K. S., Goddard, W. A., Skiff, W. M.; J. Am. Chem. Soc. 1992, 114, 10024, incorporated herein by reference) is used as a lower level theory. The UFF atom types for Si, O, Al are specified as Si3, O_3_z, Al3, respectively.

There are several examples in open literature about the quantitative accuracy of the method for estimating adsorption energy of various hydrocarbon molecules in the zeolite framework (see Kasuriya, S., Namuangruk, S., Treesukol, P., Tirtowidjojo, M., and Limtrakul, J.; J. Catal. 2003, 219, 320; and Pantu, P., Boekfa, B., Limtrakul, J.; J. Mol. Cat. A 2007, 277, 171, each incorporated herein by reference). These calculations are reproducible.

To conduct the thermochemical analysis of the molecular structures, we evaluate using the harmonic vibrational frequencies calculated using the same molecular model and level of theory. For the intermediates involving the zeolite site, rotational and translational terms of entropy (S) are neglected while calculating the entropy. For gas phase species (adsorbates), all degrees of freedom have been accounted for while calculating entropy. During the adsorption process, the molecule (adsorbate) is expected to lose its rotational and translational degrees of freedom.

Free energy of adsorption (ΔG) of molecule (adsorbate) A in zeolite Z is calculated as:

$$^T\Delta G_{Ads}^{A} = \Delta H_{Ads}^{A} - T\Delta S_{Ads}^{A}$$

wherein $\Delta H_{Ads}^{A} = H^{A+Zeolite} - H^{A} - H^{Zeolite}$ and $\Delta S_{Ads}^{A} = S^{A+Zeolite} - S^{A} - S^{Zeolite}$.

Similarly, for adsorption of two molecules A and B (co-adsorption):

$$^T\Delta G_{Co\text{-}Ads}^{A+B} = \Delta H_{Co\text{-}Ads}^{A+B} - T\Delta S_{Co\text{-}Ads}^{A+B}$$

wherein $\Delta H_{Co\text{-}Ads}^{A+B} = H^{A+B+Zeolite} - H^{A} - H^{B} - H^{Zeolite}$ and $\Delta S_{Co\text{-}Ads}^{A+B} = S^{A+B+Zeolite} - S^{A} - S^{B} - S^{Zeolite}$.

The catalytic conversion process of the present invention uses the improved selected catalyst composition. In description of the process, the term "liquid or partial liquid phase" means that the reaction mixture comprises greater than or equal to 10 volume % liquid, for example greater than or equal to 30 volume % liquid, up to 100 volume % liquid.

Methods for producing catalyst compositions to be evaluated by the present method, and if selected, for use in the present catalytic conversion process comprise those taught in the publications listed herein and incorporated herein by reference, modified only by adjustments designed to insure the final catalyst to have maximum MASF and optionally OOSF. For example, U.S. Pat. No. 4,954,325 describes crystalline MCM-22 and catalyst comprising same; U.S. Pat. No. 5,236,575 describes crystalline MCM-49 and catalyst comprising same; U.S. Pat. No. 5,362,697 describes crystalline MCM-56 and catalyst comprising same; and U.S. Pat. No. 6,756,030 describes crystalline UZM-8 and catalyst comprising same. In adjusting the method to form the catalyst required for use herein, care is taken to do so such that the final catalyst product has the highest possible MASF and optionally OOSF.

The term "aromatic" in reference to the alkylatable aromatic compounds which may be useful as feedstock herein is to be understood in accordance with its art-recognized scope. This includes alkyl substituted and unsubstituted mono- and polynuclear compounds. Compounds of an aromatic character that possess a heteroatom are also useful provided they do not act as catalyst poisons under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic compounds include benzene, naphthalene, anthracene, naphthacene, perylene, coronene, and phenanthrene, with benzene being preferred.

Generally the alkyl groups that can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, iso-hexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethyllanthracene; 2-methylanthracene; o-methylanthracene; 9,10-dimethylphenanthrene; and 3-methyl-phenanthrene. Higher molecular weight alkylaromatic compounds can also be used as starting materials and include aromatic organics such as are produced by the alkylation of aromatic organics with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing a mixture of benzene, toluene and/or xylene constitutes a useful feed for the alkylation process of this invention.

The alkylating agents that may be useful in the process of this invention include olefins, such as ethylene and propylene; alcohols (inclusive of monoalcohols, dialcohols, trialcohols, etc.), such as methanol, ethanol and the propanols; aldehydes, such as formaldehyde, acetaldehyde and propionaldehyde; and alkyl halides such as methyl chloride, ethyl chloride and the propyl chlorides, and so forth.

Mixtures of light olefins are useful as alkylating agents in the alkylation process of this invention. Accordingly, mixtures of ethylene and propylene which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Non-limiting examples of reaction products that may be obtained from the catalytic conversion process of the present invention include ethylbenzene from the reaction of benzene with ethylene, cumene from the reaction of benzene with propylene, ethyltoluene from the reaction of toluene with ethylene and cymenes from the reaction of toluene with propylene. Particularly preferred process mechanisms of the invention relate to the production of cumene by the alkylation of benzene with propylene, and production of ethylbenzene by the alkylation of benzene with ethylene.

The reactants for the present improved catalytic conversion process can be in partially or completely liquid phase and can be neat, i.e., free from intentional admixture or dilution with other material, or they can be brought into contact with the required catalyst composition with the aid of carrier gases or diluents such as, for example, hydrogen or nitrogen.

The improved catalytic conversion process of this invention may be conducted such that the reactants, i.e., the alkylatable aromatic compound and the alkylating agent, are brought into contact with the selected catalyst in a suitable reaction zone such as, for example, in a flow reactor containing a fixed bed of the selected catalyst composition, under effective alkylation conditions. Such conditions include a temperature of from about 100° C. to less than about 300° C., preferably from about 100° C. to about 200° C., a pressure from about 100 psig (690 kPa) to about 600 psig (4140 kPa), preferably from about 100 psig (690 kPa) to about 450 psig (3102 kPa), a molar ratio of alkylatable aromatic compound to alkylating agent of from about 0.1:1 to about 50:1, preferably from about 0.5:1 to about 10:1, and a feed weight hourly space velocity (WHSV) based on the alkylating agent of from about 0.1 to 500 $hr^{-1}$, preferably from about 0.5 to about 100 $hr^{-1}$.

When benzene is alkylated with ethylene to produce ethylbenzene, the alkylation reaction is preferably carried out in the liquid phase under conditions including a temperature of from about 150° C. to less than about 300° C., preferably from about 150° C. to about 200° C.; a pressure from about 250 psig (1720 kPa) to about 600 psig (4140 kPa), preferably from about 250 psig (1720 kPa) to about 450 psig (3102 kPa); a weight hourly space velocity (WHSV) based on the ethylene alkylating agent of from about 0.1 to about 20 $hr^{-1}$, preferably from about 0.5 to about 6 $hr^{-1}$; and a ratio of benzene to ethylene in the alkylation reactor of from about 0.5:1 to about 30:1 molar, preferably from about 1:1 to about 10:1 molar.

When benzene is alkylated with propylene to produce cumene, the reaction may also take place under liquid phase conditions including a temperature of from about 100° C. to less than about 200° C.; a pressure from about 100 psig (689 kPa) to about 500 psig (3450 kPa), preferably from about 100 psig (689 kPa) to about 450 psig (3102 kPa); a weight hourly space velocity (WHSV) based on propylene alkylating agent of from about 0.1 $hr^{-1}$ to about 250 $hr^{-1}$, preferably from about 1 $hr^{-1}$ to about 50 $hr^{-1}$; and a ratio of benzene to propylene in the alkylation reactor of from about 0.5:1 to about 30:1 molar, preferably from about 1:1 to about 10:1 molar.

The catalyst compositions which may be evaluated by the present method and, if selected, used in the present improved catalytic conversion process comprise, as non-limiting examples, a crystalline molecular sieve having an MWW structure type such as, for example, those having an X-ray diffraction pattern including d-spacing maxima at 12.4±0.25, 6.9±0.15, 3.57±0.07 and 3.42±0.07 Angstroms. Examples of MWW structure type materials include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in U.S. Pat. No. 6,231,751); ITQ-30 (described in WO 2005-118476); MCM-36 (described in U.S. Pat. No. 5,250,277); MCM-49 (described in U.S. Pat. No. 5,236,575); MCM-56 (described in U.S. Pat. No. 5,362,697); and UZM-8

(described in U.S. Pat. No. 6,756,030). The catalyst composition selected will have the required MASF and, optionally, OOSF.

In the reaction mechanism of the present improved catalytic conversion process, the alkylation reactor effluent may contain excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

The polyalkylated products separated from the alkylation reactor effluent may be reacted with additional aromatic feed in a transalkylation reactor, separate from the alkylation reactor, over a suitable transalkylation catalyst. The transalkylation catalyst may comprise one or a mixture of crystalline molecular sieves having the structure of zeolite Beta, zeolite Y, mordenite or an MWW structure type material having an X-ray diffraction pattern including d-spacing maxima at 12.4±0.25, 6.9±0.15, 3.57±0.07 and 3.42±0.07 Angstroms.

The X-ray diffraction data used to characterize said above catalyst structures are obtained by standard techniques using the K-alpha doublet of copper as the incident radiation and a diffractometer equipped with a scintillation counter and associated computer as the collection system. Materials having the above X-ray diffraction lines include, for example, MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in U.S. Pat. No. 6,231,751); ITQ-30 (described in WO 2005-118476); MCM-36 (described in U.S. Pat. No. 5,250,277); MCM-49 (described in U.S. Pat. No. 5,236,575); and MCM-56 (described in U.S. Pat. No. 5,362,697).

The catalyst composition for use in the present improved catalytic conversion process may include an inorganic oxide material matrix or binder. Such matrix or binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

For the improvement of the present catalytic conversion process, relative proportions of the crystalline molecular sieve and binder or matrix are not critical, so long as the catalyst composition has the required MASF and, optionally, OOSF.

The catalyst composition selected for use in the present improved catalytic conversion process, or its crystalline molecular sieve component, may or may not contain added functionalization, such as, for example, a metal of Group VI (e.g., Cr and Mo), Group VII (e.g., Mn and Re) or Group VIII (e.g., Co, Ni, Pd and Pt), or phosphorus.

Additional embodiments of the invention are disclosed in the following numbered paragraphs.

Paragraph 1. A method for selecting a catalyst composition comprising a porous crystalline material for use in a hydrocarbon conversion process, said method comprising steps of determining the Mono Alkylation Selectivity Factor of one or more catalyst compositions, and selecting a catalyst composition which has at least one active catalytic site with a Mono Alkylation Selectivity Factor greater than or equal to 0 kcal/mol±0.5 kcal/mol.

Paragraph 2. The method of Paragraph 1, wherein said selected catalyst composition has at least one active catalytic site with a Mono Alkylation Selectivity Factor greater than or equal to 3 kcal/mol±0.5 kcal/mol.

Paragraph 3. The method of any preceding Paragraph, wherein said selected catalyst composition has at least one active catalytic site with a Mono Alkylation Selectivity Factor greater than or equal to 7 kcal/mol±0.5 kcal/mol.

Paragraph 4. The method of any preceding Paragraph, further comprising steps of determining the Olefin Oligomerization Suppression Factor of one or more catalyst compositions, and selecting a catalyst composition which has at least one active catalytic site with an Olefin Oligomerization Suppression Factor greater than or equal to 5 kcal/mol±0.5 kcal/mol.

Paragraph 5. The method of Paragraph 4, wherein said selected catalyst composition has at least one active catalytic site with an Olefin Oligomerization Suppression Factor greater than or equal to 7 kcal/mol±0.5 kcal/mol.

Paragraph 6. The method of Paragraph 4, wherein said selected catalyst composition has at least one active catalytic site with an Olefin Oligomerization Suppression Factor greater than or equal to 10 kcal/mol±0.5 kcal/mol.

Paragraph 7. The method of any preceding Paragraph, wherein said Mono Alkylation Selectivity Factor (MASF) is defined by the formula:

$$\text{MASF} = {}^T\Delta G_{Co\text{-}Ads}^{Olefin+MonoAlkylated\ Aromatics} - {}^T\Delta G_{Co\text{-}Ads}^{Olefin+Aromatics}.$$

Paragraph 8. The method of Paragraph 4, wherein said Olefin Oligomerization Suppression Factor (OOSF) is defined by the formula:

$$\text{OOSF} = {}^T\Delta G_{Ads}^{Olefin} - {}^T\Delta G_{Ads}^{Aromatics}.$$

Paragraph 9. A catalyst composition comprising a porous crystalline material, said composition having at least one active catalytic site with a Mono Alkylation Selectivity Factor greater than or equal to 7.5 kcal/mol.

Paragraph 10. The catalyst composition of Paragraph 9, further having at least one active catalytic site with an Olefin Oligomerization Suppression Factor greater than or equal to 11.4 kcal/mol.

Paragraph 11. A process for catalytic conversion of feedstock comprising at least one alkylatable aromatic compound and an alkylating agent to conversion product comprising an alkylaromatic compound which comprises contacting said feedstock under catalytic conversion conditions including a molar ratio of alkylatable aromatic compound to alkylating agent of from about 0.1:1 to about 50:1, a feed weight hourly space velocity (WHSV) based on the alkylating agent of from about 0.1 to about 500 hr$^{-1}$, a temperature of from about 100° C. to less than about 300° C. and a pressure from about 100 psig (690 kPa) to about 600 psig (4140 kPa), with a catalyst composition of Paragraphs 10 or 11, or with the catalyst composition selected by the method of Paragraphs 1-9.

Paragraph 12. The process of Paragraph 11, wherein the catalyst composition comprises an aluminosilicate zeolite.

Paragraph 13. The process of Paragraph 12, wherein the aluminosilicate zeolite having an MWW structure type.

Paragraph 14. The process of Paragraph 13, wherein said aluminosilicate zeolite having MWW structure type is selected from the group consisting of MCM-22, PSH-3, SSZ-25, ERB-1, ITQ-1, ITQ-2, ITQ-30, MCM-36, MCM-49, MCM-56, UZM-8 and combinations thereof.

EXAMPLES

In exemplifying the present invention, computed results for alkylation of benzene by propylene for MWW, FAU, and BEA classes of materials, in particular MCM-22, Faujasite and zeolite Beta, respectively, are summarized in Table 1. The Table shows the specific catalyst composition attribute values (MASF and OOSF) for these three framework types. In Table 1, Gibbs free energy of adsorption of propylene, benzene, cumene on the MWW, FAU and BEA materials is shown. Also included are free energy of co-adsorption of benzene-propylene, and cumene-propylene.

TABLE 1

| Zeolite | Molecules | ΔE kcal/mol | ΔH kcal/mol | ΔS cal/mol | ΔG 130° C. |
|---|---|---|---|---|---|
| MCM-22 | Propylene | −12.9 | −11.4 | −32.2 | 1.6 |
| | Benzene | −25.0 | −23.1 | −35.6 | −8.8 |
| | Cumene | −29.9 | −27.9 | −41.9 | −11.0 |
| | Propylene + Benzene | −37.1 | −34.1 | −74.5 | −4.1 |
| | Propylene + Cumene | −35.1 | −31.3 | −86.0 | 3.4 |
| | MASF | | | | 7.5 |
| | OOSF | | | | 10.4 |
| Beta | Propylene | −14.0 | −13.0 | −34.2 | 0.8 |
| | Benzene | −19.1 | −17.9 | −34.3 | −4.0 |
| | Cumene | −28.5 | −27.2 | −37.3 | −12.2 |
| | Propylene + Benzene | −33.4 | −31.1 | −69.4 | −3.1 |
| | Propylene + Cumene | −40.8 | −38.1 | −80.5 | −5.7 |
| | MASF | | | | −2.6 |
| | OOSF | | | | 4.8 |
| Faujasite | Propylene | −12.1 | −11.1 | −33.7 | 2.5 |
| | Benzene | −14.7 | −13.5 | −33.0 | −0.2 |
| | Cumene | −22.3 | −21.1 | −38.2 | −5.7 |
| | Propylene + Benzene | −30.8 | −28.8 | −67.2 | −1.7 |
| | Propylene + Cumene | −38.7 | −36.5 | −73.0 | −7.1 |
| | MASF | | | | −5.4 |
| | OOSF | | | | 2.7 |

Further in exemplifying the present invention, computed results for comparison of Gibbs free energy of co-adsorption of benzene-ethylene, ethylbenzene-ethylene, cumene-propylene in MWW and FAU classes of materials, in particular MCM-22 and Faujasite, are summarized in Table 2. This table shows the specific catalyst composition attribute values (MASF and OOSF) for these three framework types.

TABLE 2

| Zeolite | Molecules | ΔE kcal/mol | ΔH kcal/mol | ΔS kcal/mol | ΔG 180° C. |
|---|---|---|---|---|---|
| MCM-22 | Ethylene | −10.5 | −9.0 | −29.3 | 4.3 |
| | Propylene | −12.9 | −11.5 | −32.2 | 3.1 |
| | Benzene | −25.0 | −23.2 | −35.6 | −7.1 |
| | Ethylbenzene | −28.0 | −26.2 | −41.9 | −7.2 |
| | Cumene | −29.9 | −28.0 | −41.9 | −9.0 |
| | Ethylene + Benzene | −34.9 | −32.1 | −70.7 | 0.0 |
| | Ethylene + Ethylbenzene | −35.7 | −32.5 | −78.4 | 3.0 |
| | MASF | | | | 3.0 |
| | OOSF | | | | 11.4 |
| Faujasite | Ethylene | −10.1 | −9.2 | −30.9 | 4.8 |
| | Propylene | −12.1 | −11.2 | −33.7 | 4.1 |
| | Benzene | −14.7 | −13.6 | −33.0 | 1.3 |
| | Ethylbenzene | −20.1 | −19.0 | −37.7 | −1.9 |
| | Cumene | −22.3 | −21.2 | −38.2 | −3.9 |
| | Ethylene + Benzene | −28.7 | −26.7 | −64.5 | 2.5 |
| | Ethylene + Ethylbenzene | −33.1 | −31.1 | −65.8 | −1.3 |
| | MASF | | | | −3.8 |
| | OOSF | | | | 3.5 |

Table 2 summarizes analogous results for the alkylation of benzene using ethylene to form ethylbenzene ("EB"). The results show that the ΔG for co-adsorption of ethylene and benzene on MWW ($^T\Delta G_{Co\text{-}Ads}^{Ethylene+Benzene}$) is thermodynamically more favorable compared to ΔG for co-adsorption of ethylene and ethylbenzene ($^T\Delta G_{Co\text{-}Ads}^{Ethylene+EB}$) on MCM-22. The opposite is true for Faujasite. Thus, based on the required catalyst composition attributes, MCM-22 with an MASF value of 3.0 is expected to be more selective than Faujasite with an MASF value of −3.8. This is consistent with the experimental observation that MCM-22 is a more selective material for alkylation of benzene with ethylene.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit within same are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:
1. A process for catalytic conversion of a feedstock comprising at least one alkylatable aromatic compound and an alkylating agent to a conversion product comprising an alkylaromatic compound, said process comprising:
   determining a Mono Alkylation Selectivity Factor of one or more catalyst compositions, and selecting a catalyst composition which has at least one active catalytic site with said Mono Alkylation Selectivity Factor greater than or equal to 0 kcal/mol±0.5 kcal/mol, wherein said Mono Alkylation Selectivity Factor is defined by the formula:

$$MASF = {}^T\Delta G_{Co\text{-}Ads}^{Olefin+MonoAlkylated\ Aromatics} - {}^T\Delta G_{Co\text{-}Ads}^{Olefin+Aromatics},$$

wherein MASF represents Mono Alkylation Selectivity Factor, T is Temperature in °C., ${}^T\Delta G_{Co\text{-}Ads}^{Olefin+MonoAlkylatedAromatics}$ is free energy of co-adsorption of olefin and monoalkylated aromatics in kcal/mol, and ${}^T\Delta G_{Co\text{-}Ads}^{Olefin+Aromatics}$ is free energy of co-adsorption of olefin and aromatics in kcal/mol;

contacting said feedstock under catalytic conversion conditions including a molar ratio of said alkylatable aromatic compound to said alkylating agent of from about 0.1:1 to about 50:1, a feed weight hourly space velocity (WHSV) based on said alkylating agent of from about 0.1 to about 500 hr$^{-1}$, a temperature of from about 100° C. to less than about 300° C. and a pressure from about 100 psig (690 kPa) to about 600 psig (4140 kPa), with the selected catalyst composition so as to form a conversion product comprising an alkylaromatic compound.

2. The process of claim 1, wherein said porous crystalline material is an aluminosilicate zeolite.

3. The process of claim 2, wherein said porous crystalline material comprises an MWW structure type.

4. The process of claim 3, wherein said porous crystalline material is selected from the group consisting of MCM-22, PSH-3, SSZ-25, ERB-1, ITQ-1, ITQ-2, ITQ-30, MCM-36, MCM-49, MCM-56, UZM-8 and combinations thereof.

5. The process of claim 1, wherein said selected catalyst composition has at least one active catalytic site with a Mono Alkylation Selectivity Factor greater than or equal to 3 kcal/mol±0.5 kcal/mol, or greater than or equal to 7 kcal/mol±0.5 kcal/mol.

6. The process of claim 1, wherein said selected catalyst composition further has at least one active catalytic site with an Olefin Oligomerization Suppression Factor (OOSF) greater than or equal to 5 kcal/mol±0.5 kcal/mol defined by the formula:

$$OOSF = {}^T\Delta G_{Ads}^{Olefin} + {}^T\Delta G_{Ads}^{Aromatics},$$

wherein OOSF represents Olefin Oligomerization Suppression Factor, ${}^T\Delta G_{Ads}^{olefin}$ is free energy of adsorption of olefin in kcal/mol, and ${}^T\Delta G_{Ads}^{Aromatics}$ is free energy of adsorption of aromatics in kcal/mol.

7. The process of claim 6, wherein said selected catalyst composition further has at least one active catalytic site with an Olefin Oligomerization Suppression Factor greater than or equal to 7 kcal/mol±0.5 kcal/mol, or greater than or equal to 10 kcal/mol±0.5 kcal/mol.

8. The process of claim 1, wherein said alkylatable aromatic compound comprises benzene and said alkylating agent comprises ethylene, said conversion product comprises ethylbenzene, and said conversion conditions include a temperature of from about 150° C. to less than about 300° C., a pressure from about 250 psig (1720 kPa) to about 600 psig (4140 kPa), a weight hourly space velocity (WHSV) based on said ethylene alkylating agent of from about 0.1 to about 20 hr$^{-1}$, and a ratio of benzene to ethylene in an alkylation reactor of from about 0.5:1 to about 30:1 molar.

9. The process of claim 8, wherein said porous crystalline material comprises a crystalline molecular sieve having an X-ray diffraction pattern including d-spacing maxima at 12.4±0.25, 6.9±0.15, 3.57±0.07 and 3.42±0.07 Angstroms.

10. The process of claim 8, wherein said selected catalyst composition further has at least one active catalytic site with an Olefin Oligomerization Suppression Factor (OOSF) greater than or equal to 5 kcal/mol±0.5 kcal/mol defined by the formula:

$$OOSF = {}^T\Delta G_{Ads}^{Olefin} - {}^T\Delta G_{Ads}^{Aromatics};$$

wherein OOSF represents Olefin Oligomerization Suppression Factor, ${}^T\Delta G_{Ads}^{olefin}$ is free energy of adsorption of olefin in kcal/mol, and ${}^T\Delta G_{Ads}^{Aromatics}$ is free energy of adsorption of aromatics in kcal/mol.

11. The process of claim 1, wherein said alkylatable aromatic compound comprises benzene and said alkylating agent comprises propylene, said conversion product comprises cumene, and said conversion conditions include a temperature of from about 100° C. to less than about 200° C., a pressure from about 100 psig (689 kPa) to about 500 psig (3450 kPa), a weight hourly space velocity (WHSV) based on propylene alkylating agent of from about 0.1 hr$^{-1}$ to about 250 hr$^{-1}$, and a ratio of benzene to propylene in an alkylation reactor of from about 0.5:1 to about 30:1 molar.

12. The process of claim 11, wherein said porous crystalline material comprises a crystalline molecular sieve having an X-ray diffraction pattern including d-spacing maxima at 12.4±0.25, 6.9±0.15, 3.57±0.07 and 3.42±0.07 Angstroms.

13. The process of claim 11, wherein said selected catalyst composition further has at least one active catalytic site with an Olefin Oligomerization Suppression Factor (OOSF) greater than or equal to 5 kcal/mol±0.5 kcal/mol defined by the formula:

$$OOSF = {}^T\Delta G_{Ads}^{Olefin} - {}^T\Delta G_{Ads}^{Aromatics};$$

wherein OOSF represents Olefin Oligomerization Suppression Factor, ${}^T\Delta G_{Ads}^{olefin}$ is free energy of adsorption of olefin in kcal/mol, and ${}^T\Delta G_{Ads}^{Aromatics}$ is free energy of adsorption of aromatics in kcal/mol.

14. The process of claim 1, wherein said alkylatable aromatic compound is selected from the group consisting of benzene, cumene, naphthalene, anthracene, naphthacene, perylene, coronene, phenanthrene and combinations thereof.

15. The process of claim 14, wherein said porous crystalline material comprises a crystalline molecular sieve having an X-ray diffraction pattern including d-spacing maxima at 12.4±0.25, 6.9±0.15, 3.57±0.07 and 3.42±0.07 Angstroms.

16. The process of claim 14, wherein said selected catalyst composition further has at least one active catalytic site with an Olefin Oligomerization Suppression Factor (OOSF) greater than or equal to 5 kcal/mol±0.5 kcal/mol defined by the formula:

$$OOSF = {}^T\Delta G_{Ads}^{Olefin} - {}^T\Delta G_{Ads}^{Aromatics};$$

wherein OOSF represents Olefin Oligomerization Suppression Factor, ${}^T\Delta G_{Ads}^{Olefin}$ is free energy of adsorption of olefin in kcal/mol, and ${}^T\Delta G_{Ads}^{Aromatics}$ is free energy of adsorption of aromatics in kcal/mol.

17. The process of claim 1, wherein the selected catalyst composition has at least one active catalytic site with a Mono Alkylation Selectivity Factor (MASF) greater than or equal to 7.5 kcal/mol.

18. The process of claim 17, wherein said catalyst composition further has at least one active catalytic site with an Olefin Oligomerization Suppression Factor (OOSF) greater than or equal to 11.4 kcal/mol defined by the formula:

$$OOSF = {}^T\Delta G_{Ads}^{olefin} - {}^T\Delta G_{Ads}^{Aromatics},$$

wherein T is temperature in °C., and ${}^T\Delta G_{Ads}^{Aromatics}$ is free energy of adsorption of aromatics in kcal/mol.

\* \* \* \* \*